United States Patent
Takahashi (12)

(10) Patent No.: US 6,595,913 B2
(45) Date of Patent: Jul. 22, 2003

(54) CABLE STRUCTURE IN ELECTRONIC ENDOSCOPE

(75) Inventor: Kazuaki Takahashi, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 42 days.

(21) Appl. No.: 09/946,539

(22) Filed: Sep. 6, 2001

(65) Prior Publication Data

US 2002/0028982 A1 Mar. 7, 2002

(30) Foreign Application Priority Data

Sep. 7, 2000 (JP) ........................................ 2000-270952
Sep. 29, 2000 (JP) ........................................ 2000-298210

(51) Int. Cl.$^7$ ................................................ A61B 1/05
(52) U.S. Cl. ........................................ 600/110; 600/130
(58) Field of Search ................................ 600/109, 110, 600/129, 130; 174/75 C

(56) References Cited

U.S. PATENT DOCUMENTS

| | | | | |
|---|---|---|---|---|
| 5,873,816 A | * | 2/1999 | Kagawa et al. | 600/134 |
| 5,876,326 A | * | 3/1999 | Takamura et al. | 600/110 |
| 5,879,285 A | * | 3/1999 | Ishii | 600/110 |
| 6,239,373 B1 | * | 5/2001 | Sato et al. | 174/75 C |
| 6,395,977 B1 | * | 5/2002 | Yamamoto | 174/36 |

FOREIGN PATENT DOCUMENTS

JP     A 6-285020     10/1994

* cited by examiner

Primary Examiner—John P. Leubecker
Assistant Examiner—Aaron Roane
(74) Attorney, Agent, or Firm—Oliff & Berridge, PLC

(57) ABSTRACT

A lead is connected to a shield through a notch formed on a sheathing of the shield so that the connecting part between the shield and the lead is contained within the notch. A sheathing of the lead can be directly connected over the sheathing of the shield, and at the same time the end of the shield and the end of the lead can be prevented from directly contacting with the core leads. Thus, the connecting part is not bulky, and the cable can be thinner.

8 Claims, 6 Drawing Sheets

F I G. 4
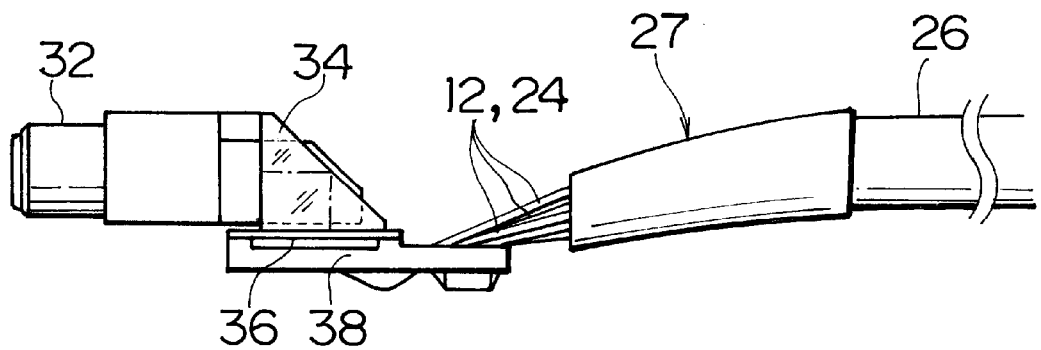

CABLE STRUCTURE IN ELECTRONIC ENDOSCOPE

BACKGROUND OF THE INVENTION

1. Field of the Invention

The present invention relates to a cable structure in an electronic endoscope, particularly to a cable structure in an electronic endoscope in which a video signal is outputted from a solid-state imaging device provided in a distal end assembly of the electronic endoscope.

2. Description of the Related Art

An electronic endoscope has a solid-state imaging device such as a charge-coupled device (CCD), which is arranged behind an imaging optical system provided within a distal end assembly of an insertion part. The CCD is mounted on a CCD board made of ceramics and the like, and a number of leads are connected to terminals provided on the CCD board.

A set of the leads composes a multi-core cable, which comprises the leads (now referred to as core leads), a conductive meshed shield and an outside insulator or a sheathing. The multi-core cable is connected with a processor, which processes a video signal outputted from the CCD and transmitted through the core leads, and the subject image is displayed on a monitor device.

As seen from FIG. 8, the conventional multi-core cable is constructed in which an insulator tape 9 is wound around the core leads 1, and further the core leads 1 are covered with the conductive meshed shield 2 and an outside insulator or a sheathing 3. The meshed shield 2 is connected with a ground lead 4 within the insertion part of the endoscope, and the sheathing 3 is connected with an outside insulator or a sheathing 5 that covers the ground lead 4 and the core leads 1.

Japanese Patent Application Publication No. 6-285020 discloses a connecting structure between the meshed shield 2 and the ground lead 4. FIG. 8 shows an applied example where the sheathing 5 is provided at the board side of the connecting part. In the applied example, the meshed shield 2 is extended from the sheathing 3 and twined, and the ground lead 4 is soldered with the twined part. Inside the connecting part of the meshed shield 2 and the ground lead 4, the core leads 1 is covered with a protection tube 6, so that the meshed shield 2 and the ground lead 4 are prevented from damaging the core leads 1 and from causing a short-circuit, due to their contact with the core leads 1 in a case where ends of the meshed shield 2 and the ground lead 4 are untwined. Moreover, two attachment tubes 7 and 8 are arranged over the connecting part between the meshed shield 2 and the ground lead 4. The protection tube 6 and the attachment tube 7 hold near the connecting part of the meshed shield 2 and the ground lead 4, and the attachment tubes 7 and 8 pinch the sheathing 5. The sheathing 3 and the sheathing 5, which have different diameters, are connected with each other by the protection tube 6 and attachment tubes 7 and 8.

Consequently, the multi-core cable is thick since the conventional cable structure requires the protection tube 6 and the attachment tubes 7 and 8.

The multi-core cable has been desired to be as thin as possible because the insertion part of the electronic endoscope already has a forceps channel, a wire guide for adjusting focus, an angle control wire, air and water supply channels, and so forth arranged therein before the multi-core cable. Spaces used for arranging the forceps channels are limited if the multi-core cable is considerably thick.

SUMMARY OF THE INVENTION

The present invention has been developed in view of the above-described circumstances, and has as its object the provision of a cable structure of an electronic endoscope with which the multi-core cable can be thinner.

In order to achieve the above-described object, the present invention is directed to a cable structure arranged in an insertion part of an electronic endoscope, the cable structure comprising: a first lead; a conductive shield member which covers the first lead; a first non-conductive covering member which covers the first lead and the shield member; a second lead which is connected to the shield member at a connecting part; and a second non-conductive covering member which covers the first lead and the second lead, an end of the second covering member being connected over an end of the first covering member, wherein: the first covering member has an opening at the connecting part so that the shield member is exposed and connected to the second lead through the opening; and the second covering member covers the end of the first covering member including the opening so as to cover the connecting part.

According to the present invention, the second lead is connected with the shield member through the opening formed on the first covering member, so that the connecting part between the second lead and the shield member can be contained in the opening. Therefore, the connecting part cannot be bulky and the cable structure can be thinner.

Moreover, since the connecting part between the second lead and the shield member is arranged in the opening formed on the first covering member, the second covering member can be directly connected over the first covering member, and further the end of the shield member and the end of the second lead can be prevented from directly contacting with the first lead. Hence, the conventional protection tube and attaching tubes are not required, and the cable structure can thus be thinner.

Preferably, the cable structure further comprises a heat-contractive tube which covers the first and second leads and the other end of the second covering member, the other end of the second covering member having a notch, wherein when the heat-contractive tube is contracted with heat, the other end of the second covering member is fastened with the heat-contractive tube with respect to the first and second leads.

According to the present invention, the notch is formed at the other end of the second covering member that is covered and fastened with the heat-contractive tube, and the notch is closed when the heat-contractive tube is contracted with heat. Hence, the fastened end portion of the second covering member has no wrinkles and does not warp, so that the heat-contractive tube can be thinner after the contraction.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 4 is a plan view of the structure around the distal end of a sheathing;

DETAILED DESCRIPTION OF THE PREFERRED EMBODIMENTS

Hereunder a preferred embodiment will be described in detail for a cable structure in an electronic endoscope of the present invention in accordance with the accompanying drawings.

Figure 1:
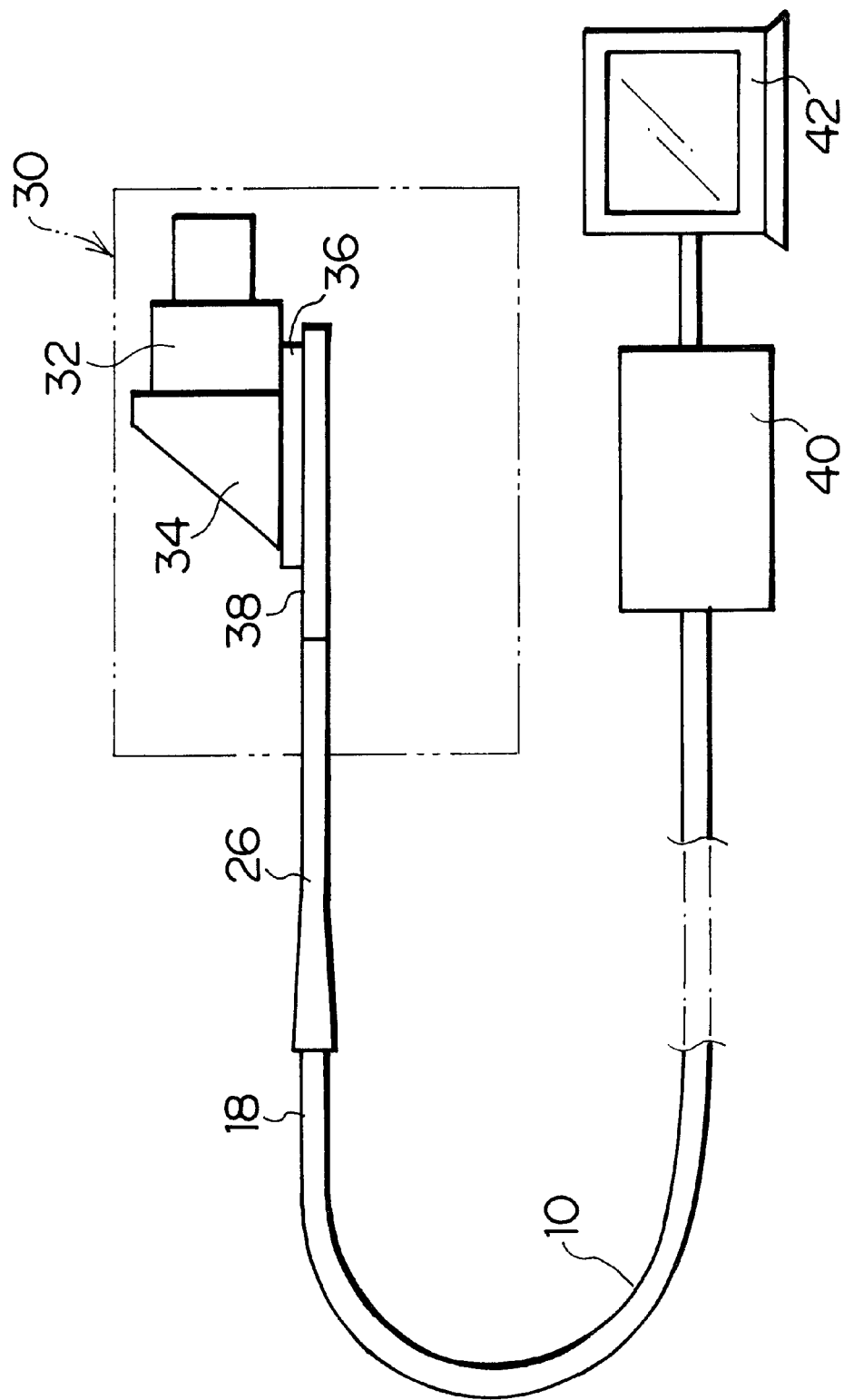
FIG. 1 is a view showing an entire electronic endoscope to which a cable structure according to an embodiment of the present invention is applied.

FIG. 1 shows an entire electronic endoscope to which a cable structure according to an embodiment of the present invention is applied. An insertion part of the electronic endoscope has a distal end assembly 30 (enlarged in FIG. 1), in which an imaging optical system 32 is arranged, and a prism 34 for bending the optical path is arranged behind the imaging optical system 32. A CCD 36 is arranged on a light-exit face of the prism 34, and the CCD 36 is mounted on a CCD board 38 made of ceramics and the like. Numbers of core leads 12 are connected to predetermined terminals formed on the CCD board 38 (see FIGS. 3 and 4).

The core leads 12 are collected within a multiple-core cable 10, and are connected with a processor 40, which processes a video signal outputted from the CCD 36 and transmitted through the core leads 12 and displays the subject image on a monitor device 42.

Figure 2:
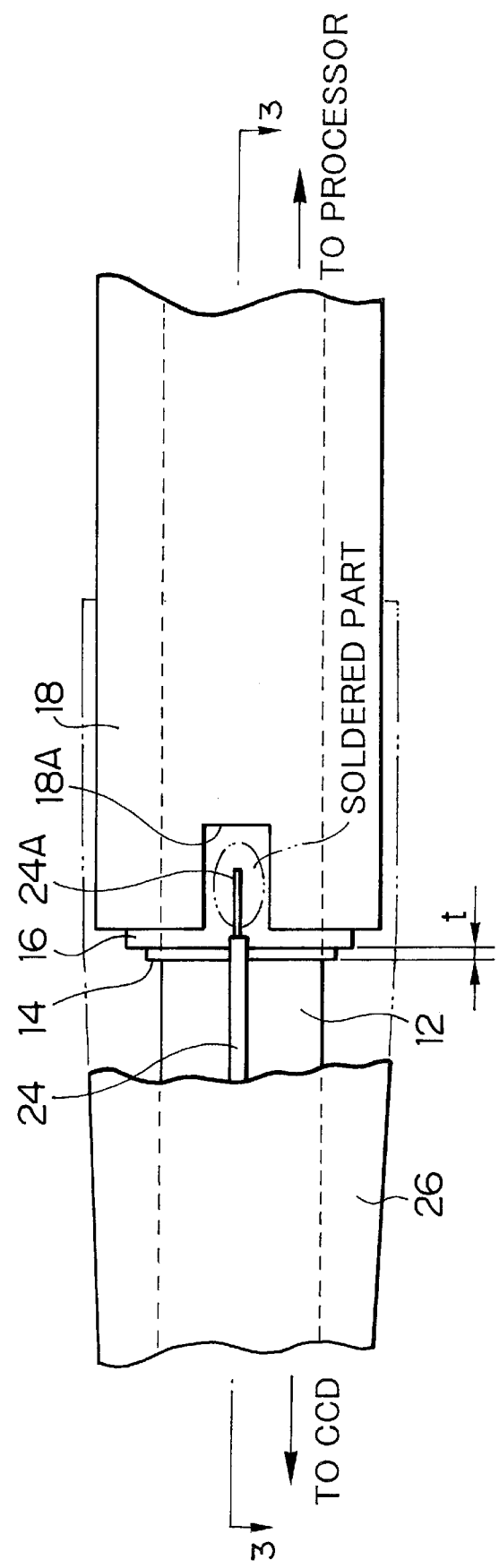
FIG. 2 is a plan view of the cable structure.
Figure 3:
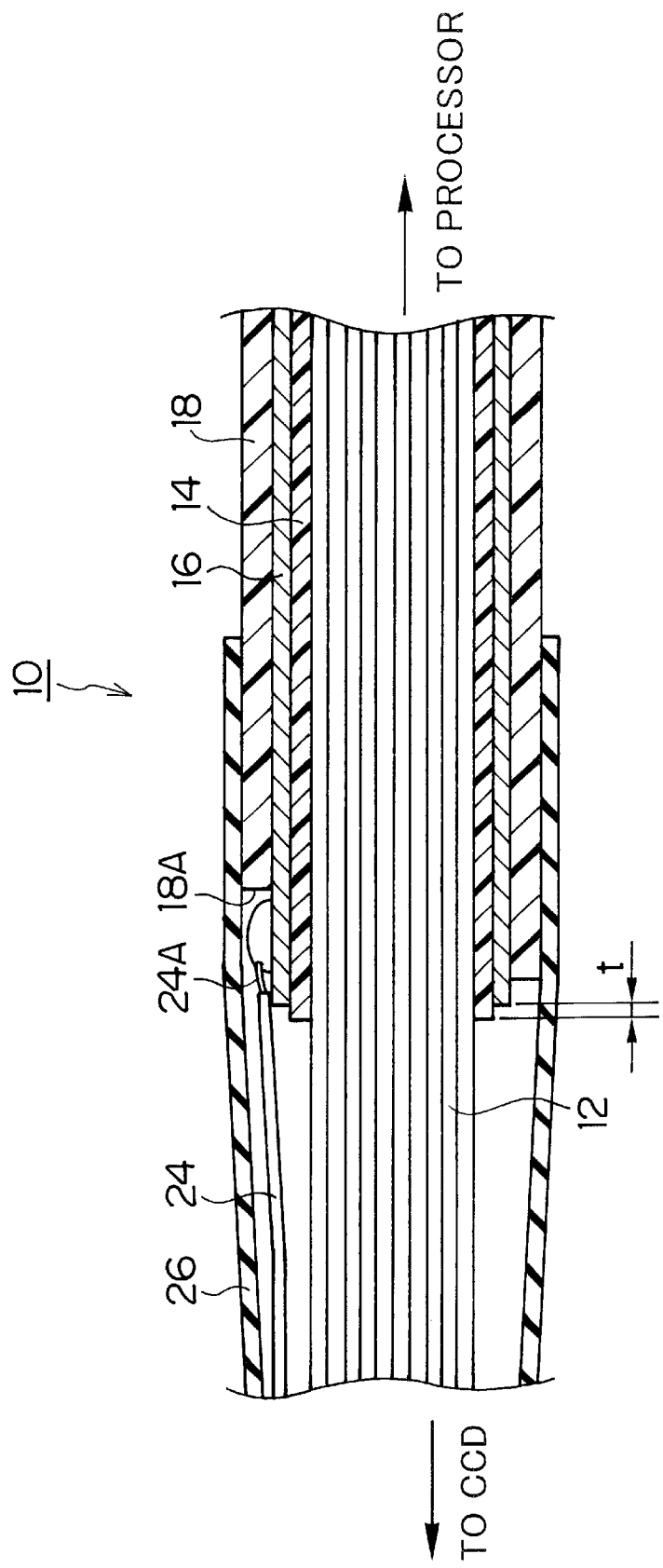
FIG. 3 is a section view of the cable structure along a line 3—3 in FIG. 2.

FIG. 2 is a plan view of the cable structure, and FIG. 3 is a section view of the cable structure along a line 3—3 in FIG. 2. As seen from FIG. 3, in the multi-core cable 10, the core leads 12 are covered with a conductive meshed shield 16 and an outside insulator or a sheathing 18 for covering the meshed shield 16. The sheathing 18 is made of insulator material such as fluoric resin and polyvinyl chloride. An insulator 14 is arranged between the core leads 12 and the meshed shield 16 so as to cover the core leads 12. More specifically, the insulator 14 can be a tape made of polyester wound around the core leads 12. The multi-core cable 10 constructed as described above has a property of short diameter, and is arranged within the distal end assembly 30 and a bending portion of the insertion part of the endoscope.

The insulator 14 is so arranged as to be slightly longer than the meshed shield 16 by a length (t), so that the end of the insulator 14 protrudes from the end of the meshed shield 16. The core leads 12 are thus prevented from being damaged and causing a short-circuit due to a direct contact of the end of the meshed shield 16 with the core leads 12.

On the side of the CCD board 38, to which the multi-core cable 10 is connected, an outside insulator or a sheathing 26 covers the core leads 12 and a ground lead 24 as shown in FIG. 3. A proximal end part 24A of the ground lead 24 is connected to the meshed shield 16, and a distal end part of the ground lead 24 is connected to a ground terminal (not shown) on the CCD board 38. The sheathing 26 comprises a silicone tube, and boron nitride powder is applied on the internal surface of the sheathing 26. The boron nitride powder is highly lubricative, has high melting point of about 3000° C., and is antioxidant and chemically stable over 1000° C. Hence, even if the boron nitride powder is exposed to hydrogen peroxide or peracetic acid, which are used to sterilize the insertion part of the endoscope, no harmful chemical is generated and the boron nitride powder keeps high capability of lubrication for a long time. Since the boron nitride powder is applied on the internal surface of the sheathing 26, the friction is reduced between the internal surface of the sheathing 26 and the outside surfaces of the leads 12 and 24. Thus, the flexibility of the sheathing 26 is improved, and the leads 12 and 24 are prevented from breaking. The multi-core cable 10 constructed as described above has a property of high elasticity, and is arranged within a flexible portion of the insertion part of the endoscope.

As seen now from FIG. 2, the connecting part between the ground lead 24 and the meshed shield 16 is constructed in which a notch 18A is formed at the end of the sheathing 18, so that the meshed shield 16 is exposed. Then, the end 24A of the ground lead 24 is soldered to the exposed part of the meshed shield 16. The meshed shield 16 is hence prevented from untwining, and a short-circuit can be prevented which is caused due to the untwined end of the meshed shield 16 damaging the core leads 12 by directly contacting with the core leads 12.

Then, the sheathing 26 is put over the end of the sheathing 18 directly, and is adhered on the sheathing 18. Thus, the notch 18A is entirely covered with the sheathing 26, and the connecting part between the meshed shield 16 and the ground lead 24 is protected by the sheathing 26.

According to the cable structure constructed in the manner as described above, the connecting part between the meshed shield 16 and the ground lead 24 is contained within the notch 18A, so that the connecting part is not bulky and the multi-core cable 10 can be thinner.

Moreover, since the connecting part is arranged within the notch 18A, the connection can be done by directly coupling the sheathing 26 onto the sheathing 18. Hence, the attachment tube is not necessary, and the multi-core cable 10 without the attachment tube can be thinner than a conventional one.

Furthermore, since the insulator 14 is arranged to be slightly longer than the meshed shield 16, and the connecting part between the meshed shield 16 and the ground lead 24 is arranged within the notch 18A the end of the meshed shield 16 and the end of the ground lead 24 can be prevented from directly contacting with the core leads 12, and thus the protection tube for preventing a short-cut is not required. Therefore, the connecting part of the multi-core cable 10 without the protection tube can be thinner than a conventional one.

Figure 5:
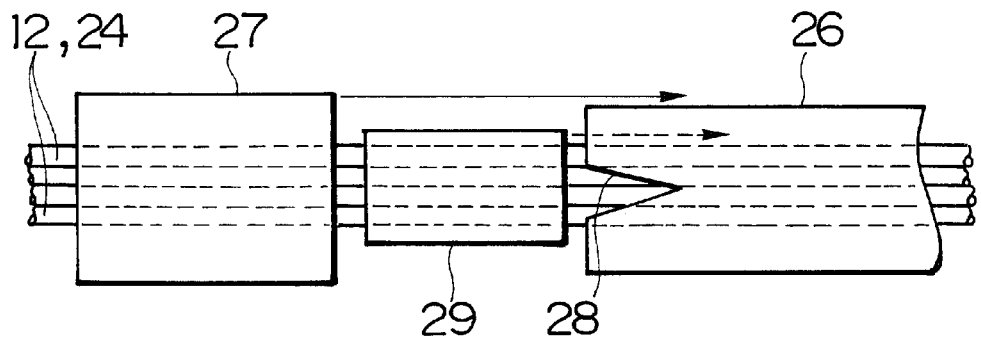
FIG. 5 is a view explaining the detailed structure around the distal end of the sheathing.
Figure 6:
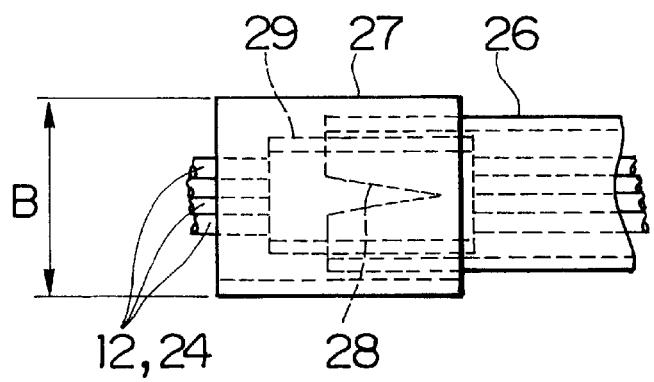
FIG. 6 is a view explaining the detailed structure around the distal end of the sheathing.
Figure 7:
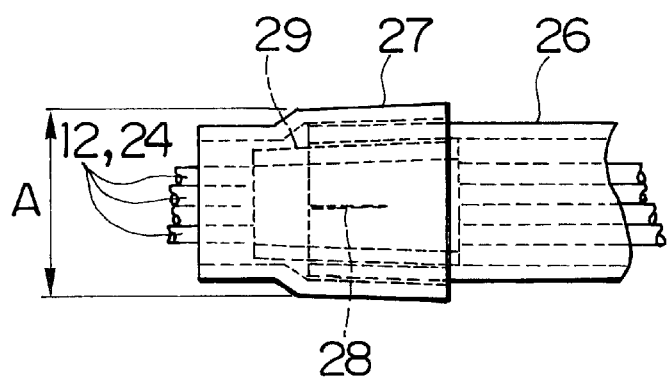
FIG. 7 is a view explaining the detailed structure around the distal end of the sheathing.
Figure 8:
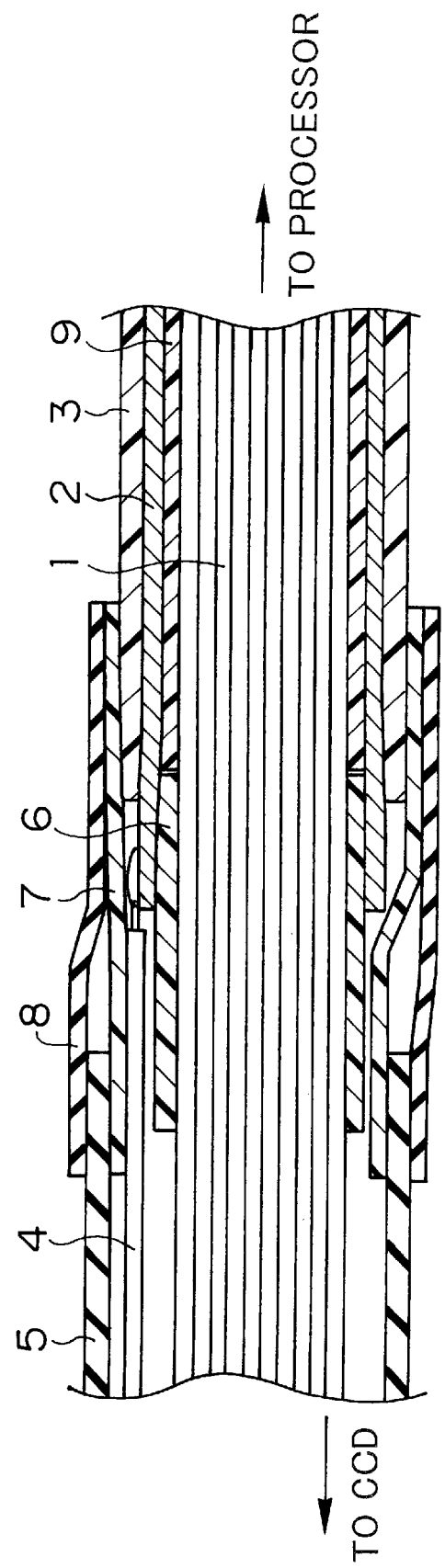
FIG. 8 is a section view showing a conventional cable structure.

FIG. 4 is a plan view showing the structure around the distal end of the sheathing 26, and FIGS. 5, 6 and 7 are views explaining the detailed structure around the distal end of the sheathing 26. As shown in FIGS. 4 and 7, the distal end of the sheathing 26 is covered and fastened with a heat-contractive tube 27 so that the sheathing 26 is prevented from slipping with respect to the leads 12 and 24.

The fastening of the distal end of the sheathing 26 on the leads 12 and 24 with the heat-contractive tube 27 is performed as follows. First, as shown in FIG. 5, a heat-contractive binding tube 29 is put over the leads 12 and 24 from the distal end side, and the proximal end of the binding tube 29 is inserted between the distal end portion of the sheathing 26 and the leads 12 and 24. Then, the heat-contractive tube 27 is put over the leads 12 and 24, the binding tube 29 and the distal end portion of the sheathing 26 from the distal end side as shown in FIG. 5. The elements are thus arranged as shown in FIG. 6. Then, the heat-contractive tube 27 is contracted with heat, and the distal end of the sheathing 26 is thus fastened with respect to the leads 12 and 24 with the heat-contractive tube 27 and the binding tube 29 as shown in FIG. 7.

A notch 28, which is V-shaped in this embodiment, is formed at the distal end portion of the sheathing 26 as shown FIGS. 5 and 6. When the heat-contractive tube 27 is contracted, the notch 28 is closed as shown in FIG. 7, and the distal end portion of the sheathing 26 is tapered off to the distal end without wrinkles or slack. Hence, the diameter A of the heat-contractive tube 27 in FIG. 7 after the contraction can be smaller than the diameter B in FIG. 6 before the contraction. If the distal end portion of the sheathing 26 has no notch or the notch is too small, wrinkles or slack may appear on the distal end portion of sheathing 26A when the heat-contractive tube 27 is contracted. A size of the notch 28 is determined so as to keep a sufficient fastening force on the distal end portion of sheathing 26, since the fastening force may be insufficient if the notch 28 is too large.

In the present embodiment, the fastening of the distal end portion of the sheathing 26 with respect to the leads 12 and 24 is described; however, the above-described structure can be applied to fastening of any end portion of non-heat-contractive tube with respect to the contents of the tube.

As described hereinabove, according to the cable structure of the electronic endoscope of the present invention, the lead is connected to the shield through the notch formed on the sheathing of the shield so that the connecting part between the shield and the lead is contained within the notch. Therefore, the connecting part is not bulky, and the cable can be thinner.

Moreover, the connecting part between the shield and the lead is arranged within the notch of the sheathing of the shield, whereby the sheathing of the lead can be directly connected over the sheathing of the shield, and at the same time the end of the shield and the end of the lead can be prevented from directly contacting with the core leads. Therefore, the protection tube and the attachment tube are not required, and the cable without such tubes can be thinner.

Furthermore, the notch is formed at the end portion of the sheathing that is covered and fastened with the heat-contractive tube, and the notch is closed when the heat-contractive tube is contracted with heat. Hence, the fastened end portion of the sheathing has no wrinkles and does not warp, so that the heat-contractive tube can be thinner after the contraction.

The present invention can be applied to any multi-core cable comprising a core lead, a shield covering the core lead, and a non-conductive sheathing covering the shield.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A cable structure arranged in an insertion part of an electronic endoscope, the cable structure comprising:

a first lead;

a conductive shield member which covers the first lead;

a first non-conductive covering member which covers the shield member covering the first lead;

a second lead which is connected to the shield member at a connecting part; and a second non-conductive covering member which covers the first lead and the second lead, an end of the second covering member being connected over an end of the first covering member, wherein:

the first covering member has an opening that forms a notch at the connecting part so that the shield member is exposed and connected to the second lead through the opening; and the second covering member covers the end of the first covering member including the opening so as to cover the connecting part.

2. The cable structure as defined in claim 1, further comprising:

an insulator member which is arranged between the first lead and the shield member so as to cover the first lead, wherein an end of the insulator member protrudes from an end of the shield member.

3. The cable structure as defined in claim 1, further comprising:

a heat-contractive tube which covers the first and second leads and the other end of the second covering member, the other end of the second covering member having a notch, wherein when the heat-contractive tube is contracted with heat, the other end of the second covering member is fastened with the heat-contractive tube with respect to the first and second leads.

4. The cable structure as defined in claim 3, wherein the notch at the other end of the second covering member is V-shaped.

5. The cable structure as defined in claim 3, further comprising a binding tube which covers the first and second leads and is covered with the other end of the second covering member and the heat-contractive tube.

6. A cable structure arranged in an insertion part of an electronic endoscope, the cable structure comprising:

a plurality of leads;

a flexible tube which covers the plurality of leads, the flexible tube having a notch at an end thereof; and a heat-contractive tube which covers the plurality of leads and the flexible tube, wherein when the heat-contractive tube is contracted with heat, the end of the flexible tube is fastened with the heat-contractive tube with respect to the plurality of leads.

7. The cable structure as defined in claim 6, wherein the notch at the end of the flexible tube is V-shaped.

8. The cable structure as defined in claim 6, further comprising a binding tube which covers the plurality of leads and is covered with the end of the flexible tube and the heat-contractive tube.

* * * * *